United States Patent
Miao et al.

(10) Patent No.: US 9,546,118 B2
(45) Date of Patent: Jan. 17, 2017

(54) CATALYST FOR THE OXIDATIVE DEHYDROGENATION OF BUTENE TO BUTADIENE AND PREPARATION PROCESS THEREOF

(71) Applicants: Changxi Miao, Shanghai (CN); Wenhai Wu, Shanghai (CN); Zhigui Fan, Shanghai (CN); Tieqiang Zeng, Shanghai (CN); Chunjing Ma, Shanghai (CN); Sheng Wu, Shanghai (CN)

(72) Inventors: Changxi Miao, Shanghai (CN); Wenhai Wu, Shanghai (CN); Zhigui Fan, Shanghai (CN); Tieqiang Zeng, Shanghai (CN); Chunjing Ma, Shanghai (CN); Sheng Wu, Shanghai (CN)

(73) Assignees: China Petroleum & Chemical Corporation, Beijing (CN); Shanghai Research Institute of Petrochemical Technology Sinopec, Shanghai (CN)

( * ) Notice: Subject to any disclaimer, the term of this patent is extended or adjusted under 35 U.S.C. 154(b) by 452 days.

(21) Appl. No.: 14/017,783

(22) Filed: Sep. 4, 2013

(65) Prior Publication Data
US 2014/0066680 A1    Mar. 6, 2014

(30) Foreign Application Priority Data
Sep. 5, 2012 (CN) .......................... 2012 1 0325042

(51) Int. Cl.
*B01J 23/78* (2006.01)
*B01J 23/80* (2006.01)
(Continued)

(52) U.S. Cl.
CPC ............... *C07C 5/48* (2013.01); *B01J 23/005* (2013.01); *B01J 23/78* (2013.01); *B01J 23/80* (2013.01);
(Continued)

(58) Field of Classification Search
None
See application file for complete search history.

(56) References Cited

U.S. PATENT DOCUMENTS

| 3,270,080 A | 8/1966 | Christmann |
| 3,450,788 A | 6/1969 | Kehl et al. |

(Continued)

FOREIGN PATENT DOCUMENTS

| CN | 1033013 A | 5/1989 |
| CN | 1072110 A | 5/1993 |

(Continued)

OTHER PUBLICATIONS

Machine Translation of Yang et al, CN 1184705 A, Sep. 1996.*

*Primary Examiner* — Colin W Slifka
(74) *Attorney, Agent, or Firm* — Finnegan, Henderson, Farabow, Garrett & Dunner, LLP (57) ABSTRACT

The present disclosure provides a catalyst for oxidative dehydrogenation of butene to butadiene, comprising at least one compound of formula $Zn_aAl_bM_cFe_eO_fZ(\alpha\text{-}Fe_2O_3)$, wherein M is at least one element chosen from Be, Mg, Ca, Sr, Mn, Ba, Cu, Co, and Ni, Z represents the percentage by weight of $\alpha\text{-}Fe_2O_3$ in the catalyst and ranges from 10% to 70%. Also provided herein is a process of preparing said catalyst and the use of said catalyst in an oxidative dehydrogenation of butene to butadiene processes.

13 Claims, 1 Drawing Sheet

(51) Int. Cl.
*B01J 23/889* (2006.01)
*C07C 5/48* (2006.01)
*B01J 37/03* (2006.01)
*B01J 23/00* (2006.01)
*B01J 35/10* (2006.01)

(52) U.S. Cl.
CPC ......... *B01J 23/8892* (2013.01); *B01J 35/1014* (2013.01); *B01J 37/031* (2013.01); *B01J 2523/00* (2013.01); *C07C 2521/02* (2013.01); *C07C 2523/02* (2013.01); *C07C 2523/06* (2013.01); *C07C 2523/72* (2013.01); *C07C 2523/745* (2013.01); *C07C 2523/75* (2013.01); *C07C 2523/755* (2013.01); *C07C 2523/80* (2013.01); *Y02P 20/52* (2015.11)

(56) References Cited

U.S. PATENT DOCUMENTS

| | | | |
|---|---|---|---|
| 3,595,810 A | 7/1971 | Kehl | |
| 3,951,869 A | 4/1976 | Baker | |
| 4,083,884 A | 4/1978 | Purdy | |
| 2012/0059208 A1* | 3/2012 | Mamedov | ................ B01J 23/80 585/625 |

FOREIGN PATENT DOCUMENTS

| | | |
|---|---|---|
| CN | 1184705 A | 6/1998 |
| DE | 2539217 A1 | 3/1976 |
| DE | 2731527 A1 | 1/1978 |

* cited by examiner

CATALYST FOR THE OXIDATIVE DEHYDROGENATION OF BUTENE TO BUTADIENE AND PREPARATION PROCESS THEREOF

The present disclosure relates to a catalyst for oxidative dehydrogenation of butene to butadiene and a preparation process thereof.

Since the catalysts for the oxidative dehydrogenation of butene to butadiene were developed in the 1960s, various metal oxide catalysts have been used for the oxidative dehydrogenation reaction of butene to butadiene. Currently, the most widely used catalysts are the spinel-type ferrite. Compared with the previous catalysts such as molybdenum, tin, antimony based catalyst, ferrite-based catalysts have the advantages of mild reaction conditions, high catalytic activity, and more specific selectivity.

$AB_2O_4$ iron spinel as the catalysts in the oxidative dehydrogenation of butene to butadiene was first reported in U.S. Pat. No. 3,270,080, wherein A is generally divalent metal ions such as $Mg^{2+}$, $Zn^{2+}$, $Co^{2+}$ and $Ni^{2+}$, and B is $Fe^{3+}$ ion. But the performance of $AB_2O_4$ iron-spinel catalysts is far from steady. It has been found that the introduction of $Cr^{3+}$ can improve the stability of a catalyst (see U.S. Pat. Nos. 3,450,788 and 3,595,810).

Lanzhou institute of Chemical Physics has reported the experimental results of supported ($SiO_2$) $ZnCrFeO_4$ type or unsupported $Zn_aCr_bFe_cO_4$ type catalysts (wherein a=1, b=0.25~1, c=1~1.75, b+c=2) (Petrochemicals Technology, 1979, 731) in three Chinese patent documents, CN1033013A (the catalysts having a general formula as $A_a^{2+}B_b^{2+}C_{c3}^{+}Fe_d^{3+}O_4 \cdot X[\alpha(\gamma)\text{-}Fe_2O_3]$, wherein A represents Zn, Mg, etc., B represents Ca, Ba, Sr, Ni, etc., C represents Cr, Ni, Bi, La, Ce, Pr, Nd, Sm, Eu, Dy and Er, etc., and wherein a=0~1.0, b=0~1.0, c=0.01~0.8, d=1.2~2.0, X=10~60% (by weight)); CN1072110A (the catalysts having a general formula as $A_a^{2+}B_b^{2+}Fe_2O_4 \cdot Z[\alpha\text{-}Fe_2O_3]$, wherein A is selected from the group consisting of Zn, Mg and Cd, B is selected from the group consisting of Ba, Ca, Zn, Ni and Mg, and wherein 0.0<a<1.0, 0.0<b<1.0, a+b=1, Z=10~70% (by weight)); and CN1184705A (the catalysts having a structure formula as $A_a^{2+}B_b^{2+}C_c^{2+}Fe_2O_4 \cdot X[\alpha\text{-}Fe_2O_3]$, wherein A is Zn, B is one or two elements selected from the group consisting of Mg, Ca, Sr and Ba, C is one element selected from Ni or Co, a=0.1~0.9, b=0.01~0.1, a+b+c=1, X=15~65% (by weight))).

Although the catalysts disclosed in those documents have provided certain economic benefits in industrial applications, the activity of the catalysts and the selectivity of the desired products are not high. In addition, some carbon deposits are generated on the catalysts in the reactors during the reaction processes, thereby resulting in the decrease of the catalytic activity with the operation time prolonged.

Accordingly, one aspect of the present disclosure is to provide a catalyst with high catalytic activity and selectivity of the desired product and good catalyst stability for oxidative dehydrogenation of butene to butadiene.

Provided herein is a catalyst for the oxidative dehydrogenation of butene to butadiene comprising at least one compound of a general structural formula; $Zn_aAl_bM_cFe_eO_f \cdot Z(\alpha\text{-}Fe_2O_3)$, wherein M is at least one element chosen from Be, Mg, Ca, Sr, Mn, Ba, Cu, Co, and Ni; Z represents the percentage by weight of $\alpha\text{-}Fe_2O_3$ in the catalyst and is ranging from 10% to 70%; wherein b is not zero, and when b is 1, a ranges from 0 to 10 (i.e., 0≤a≤10), c is larger than zero and less than or equal to 4 (i.e., 0<c≤4), e ranges from 3 to 25 (i.e., 3≤e≤25), f is greater than 4.5 and equal to or less than 48 (i.e., 4.5<f≤48); and the chemical valence states of Zn, Al, M, Fe and O in the catalyst are +2, +3, +2, +3 and −2, respectively.

In addition, it would be known by those skilled in the art that the relation to be met among the above subscripts is 2a+3b+2c+3e=2f.

In some embodiments of the present disclosure, the catalyst comprises a spinel crystal phase and an $\alpha\text{-}Fe_2O_3$ crystal phase, and the specific surface area of the catalyst ranging from 1 $m^2/g$ to 80 $m^2/g$.

In some embodiments, the catalysts comprising at least one compound of the formula $Zn_aAl_bM_cFe_eO_f \cdot Z(\alpha\text{-}Fe_2O_3)$, wherein M is at least two elements chosen from Be, Mg, Ca, Sr, Mn, Ba, Cu, Co, and Ni. Such catalysts can have higher selectivity to the desired product in the catalytic oxidative dehydrogenation reaction of butene to butadiene than the catalyst of formula $Zn_aAl_bM_cFe_eO_f \cdot Z(\alpha\text{-}Fe_2O_3)$, in which M is only one metallic element.

In some embodiments, in the formula of $Zn_aAl_bM_cFe_eO_f \cdot Z(\alpha\text{-}Fe_2O_3)$, b is 1 and a≠0). That is, the catalyst comprises zinc element, which may enable higher conversion rates in the oxidative dehydrogenation reaction of butene to butadiene.

In some embodiments, in the formula of $Zn_aAl_bM_cFe_eO_f \cdot Z(\alpha\text{-}Fe_2O_3)$, b is 1 and 3≤e≤20. That is, the atomic ratio of Fe to Al ranges from 3:1 to 20:1 in the spinel structure.

In some embodiments, the catalyst comprises at least one compound of a general structural formula: $Zn_{a'}Al_{b'}M_{c'}Fe_2O_4 \cdot Z(\alpha\text{-}Fe_2O_3)$, and wherein a' ranges from 0 to 0.8 (i.e., 0≤a'≤0.8), b is larger than 0 and less than or equal to 0.5 (i.e., 0<b'≤0.5), and c' is larger than 0 and less than or equal to 0.3 (i.e., 0<c'≤0.3). In addition, one skilled in the art would understood that 2a'+3b'+2c'=2.

Also in some embodiments, in the formula of $Zn_{a'}Al_{b'}M_{c'}Fe_2O_4 \cdot Z(\alpha\text{-}Fe_2O_3)$, a' is not 0. That is, the catalyst comprises zinc element.

In some embodiments, the Temperature Programmed Desorption (TPD) spectrum of ammonia probe molecules from the catalysts provided in the present disclosure comprises a characteristic peak at desorption temperatures of 340° C. to 400° C. and full width at half maximum of 60~100° C. As non-limiting example, the TPD spectrum of ammonia probe molecules from the catalysts provided in the present disclosure comprises: (1) a characteristic peak at desorption temperatures of 170° C. to 210° C. and full width at half maximum of 70~100° C., and (2) a characteristic peak at desorption temperatures of 260° C. to 300° C. and full width at half maximum of 40~70° C.

Also in some embodiments, the catalysts for the oxidative dehydrogenation of butene to butadiene disclosed herein comprises a certain amount of aluminum element, and its TPD spectrum of ammonia probe molecules comprises a characteristic peak at the desorption temperatures of 340 to 400° C. and full width at the half maximum (FWHM) of 60~100° C.

Another aspect of the present disclosure is to provide a process for preparing the catalyst as described above, comprising (1) preparing a mixed salt solution comprising the elements of Al, M, and Fe, and with or without the element of Zn, (2) adding a base solution such as NaOH solution or ammonia solution as a precipitating agent to obtain a pH value ranging from 8 to 12 during the precipitation, and (3) ageing, drying, and calcining the precipitate from (2) to obtain finished catalyst.

In some embodiments, in the process described above, the aging temperature of the precipitate ranges from 5° C. to 80°

C., the aging time of the precipitate ranges from 0.5 hours to 48 hours, the calcination temperature of the precipitate ranges from 500° C. to 900° C., and the calcination time of the precipitate ranges from 3 hours to 72 hours.

Further in some embodiments, the aging temperature of the precipitation ranges from 10° C. to 50° C., the aging time of the precipitation ranges from 2 hours to 24 hours, and the calcination temperature of the precipitate ranges from 600° C. to 800° C.

In some embodiments, the concentration of the NaOH solution used ranges from 1 mol/L to 4 mol/L, and the total content of all the metal ions in the mixed salt solution ranges from 1 mol/L to 2 mol/L.

Further in some embodiments, after the formation of the catalyst comprising the compound of $Zn_aAl_bM_cFe_eO_f\cdot Z(\alpha\text{-}Fe_2O_3)$ or the compound of $Zn_aAl_bM_cFe_2O_4\cdot Z(\alpha\text{-}Fe_2O_3)$, additional materials such as metal oxides or the material with other crystal phases may be incorporated into the catalysts disclosed herein to improve the textural properties of the catalyst without side effects to the dehydrogenation of butene to butadiene. For example, zinc oxide or aluminum oxide maybe incorporated into the catalysts.

Another aspect of the present disclosure further provides a process for dehydrogenation of butene to butadiene comprising: adding the catalyst as described above, or the catalyst prepared by the process as described above in the oxidative dehydrogenation reaction of butene to butadiene, wherein the reaction is carried out at a temperature in a range from 300° C. to 500° C., a space velocity ranging from 200 $h^{-1}$ to 500 $h^{-1}$, a molar ratio of oxygen-butene ranging from 0.6 to 0.9, and a molar ratio of water-butene ranging from 6:1 to 20:1 with butene, oxygen-containing gas and water vapor as feedstocks. As a non-limiting example, the reaction temperature ranges from 320° C. to 380° C., the space velocity ranges from 300 $h^{-1}$ to 500 $h^{-1}$, the molar ratio of oxygen-butene ranges from 0.6 to 0.8, and the molar ratio of water-butene ranges from 6:1 to 12:1.

In some embodiments, when using the catalyst described herein to catalyze the oxidative dehydrogenation reaction of butene to butadiene, the catalyst is activated with air or steam before the reaction, such as activated with air, wherein the activation temperature ranges from 400° C. to 500° C., and the activation time ranges from 1 hour to 2 hours, Conventionally, during the butene dehydrogenation reaction process catalyzed by iron-based catalysts, $\alpha\text{-}Fe_2O_3$ is easily transformed into $Fe_2O_3$ spinet. A part of the $Fe^{3+}$ ions form $Fe_3O_4$ spinel together with adjacent $Fe^{3+}$ ions because they can't be re-oxidized after being reduced to $Fe^{2+}$ ions. As a result, the acidity or the electron accepting ability of the metal centers on the catalyst surface is decreased.

$$C_4H_8 + Fe^{3+} + O^-(\text{adsorption}) \rightarrow C_4H_6 + Fe^{2+} + H_2O$$

$$Fe^{2+} + O_2 \rightarrow Fe^{3+} + O^-(\text{adsorption})$$

$$2Fe^{3+} + 2Fe^{2+} + 4O^{2-}(\text{crystal lattice}) \rightarrow Fe_3O_4 + Fe^{2+}$$

In the present disclosure, the introduction of $Al^{3+}$ may allow the catalyst to present a more regular ferrite spinel structure, thereby improving dispersion of $\alpha\text{-}Fe_2O_3$ in the catalyst, and rendering it less likely that the structure of $\alpha\text{-}Fe_2O_3$ is transformed irrevocably into $Fe_3O_4$ spinel, which enhances the stability of the catalyst. In addition, the introduction of electron-deficient $Al^{3+}$ may also enhance the activation of olefin molecules and improve the activity of the catalyst.

In an embodiment, under the reaction conditions: a reaction temperature of 360° C., a space velocity of butene of 350 $h^{-1}$, the molar ratio of oxygen-butene is 0.7:1, and the molar ratio of water-butene is 10:1, the conversion per pass of butene may be up to 85.3%, the selectivity of butadiene may be as high as 97.5%, the yield per pass of butadiene may be up to 83.2%, and the catalyst life may be more than 6,000 hours.

EXAMPLES

The following examples further explain the present disclosure. It should be noted that in the embodiments described below, in Table 1, the corresponding Z value was measured with XRD.

Example 1

Catalyst preparation: 5.13 g of $Mg(NO_3)_2\cdot 6H_2O$, 7.51 g of $Al(NO_3)_3\cdot 9H_2O$, 14.88 g of $Zn(NO_3)_2\cdot 6H_2O$, and 212.52 g of $Fe(NO_3)_3\cdot 9H_2O$ were dissolved in 500 ml of distilled water. NaOH solution (3M) was added dropwise under quick stirring to obtain a pH value of 9.3 during the precipitation. The resulting precipitate was heated for 90 minutes at 65° C. under stirring for it to be aged, stood at room temperature for 12 hours, and then filtered. The resulting filter cake was then washed with distilled water, dried at 120° C. for 24 hours, and then placed into a muffle furnace with a furnace temperature of 700° C. and calcined for 6 hours. The resulting catalyst is denoted by A.

Figure 1:
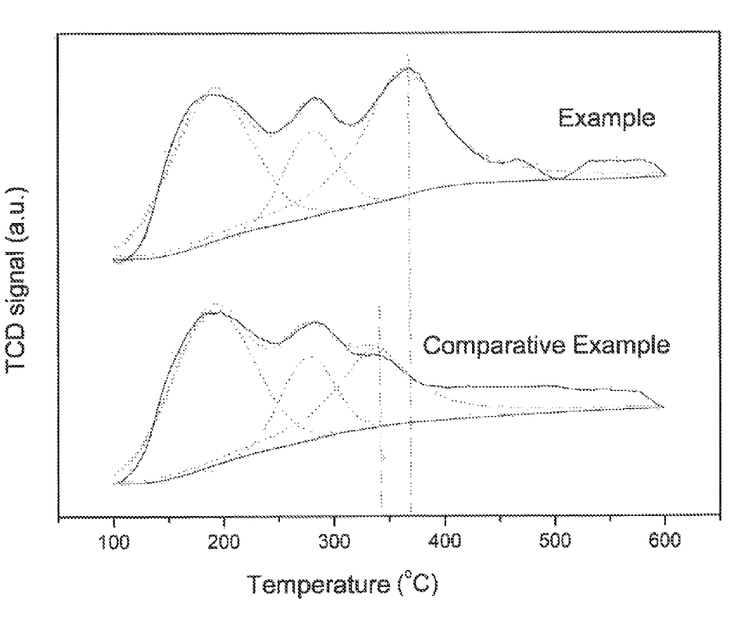
FIG. 1 shows the temperature programmed desorption spectrum of the ammonia probe molecules of the catalysts in Example 1 and Comparative Example 1 of the present disclosure.

The composition and acid sites of the catalyst are shown in Table 1 and Table 2. XRD characterization results indicate that the catalyst contains a spinel crystal phase and an $\alpha\text{-}Fe_2O_3$ crystal phase; and the temperature programmed desorption test of ammonia shows that there are enhanced acid sites on the catalyst surface, and the specific surface area of the catalyst was 12 $m^2/g$. FIG. 1 contains the Temperature-Programmed Desorption (TPD) spectrum of ammonia from the catalyst prepared in Example 1. The characteristic peak and full width at the half maximum (FWHM) shown in the TPD spectrum can be used to characterize the acid sites of the catalyst. As FIG. 1 shows, there are three ammonia desorption peaks on the TPD spectrum of the catalyst in Example 1, i.e., at desorption temperatures of 170~210° C., FWHM of 70~100° C.; desorption temperatures of 260~300° C., FWHM of 40~70° C.; and desorption temperatures of 340~400° C., FWHM of 60~100° C., respectively.

Catalyst evaluation: The catalyst was crushed, screened (taking the ones with 20-40 meshes), and activated for 1 hour with air in a fixed bed reactor at 470° C. After being cooled, the catalyst was used to catalyze the oxidative dehydrogenation reaction of butene to butadiene at a temperature of 360° C., a space velocity of 350 $h^{-1}$, a molar ratio of oxygen-butene of 0.75:1, and a molar ratio of water-butene of 10:1. The yield per pass of butadiene was 80.1%, the conversion per pass of butene was 85.9% and the selectivity of butadiene was 91.3%.

Example 2

Catalyst preparation: 5.13 g of $Mg(NO_3)_2\cdot 6H_2O$, 15.00 g of $Al(NO_3)_3\cdot 9H_2O$, 5.95 g of $Zn(NO_3)_2\cdot 6H_2O$ and 264.71 g of Fe(NO$_3$)$_3$.9H$_2$O were weighed, and the preparation process of the catalyst was the same as that in Example 1. The resulting catalyst is denoted by B.

The composition and acid sites of the catalyst are shown in Table 1 and Table 2. XRD characterization results indicated that the catalyst contained a spinel crystal phase and an α-Fe$_2$O$_3$ crystal phase. The temperature programmed desorption test of ammonia showed that there were enhanced acid sites on the catalyst surface, and the specific surface area of the catalyst was 25 m$^2$/g.

Catalyst evaluation: The evaluation conditions of the catalyst were the same as those in Example 1. The yield per pass of butadiene was 78.1%, the conversion per pass of butene was 83.3%, and the selectivity of butadiene was 93.8%.

Example 3

Catalyst preparation: Taking 3.85 g of Mg(NO$_3$)$_2$.6H$_2$O, 3.76 g of Al(NO$_3$)$_3$.9H$_2$O, 20.84 g of Zn(NO$_3$)$_2$.6H$_2$O and 180.58 g of Fe(NO$_3$)$_3$.9H$_2$O were weighed, and the preparation process of the catalyst was the same as that in Example 1. The resulting catalyst is denoted by C.

The composition and acid sites of the catalyst are shown in Table 1 and Table 2. XRD characterization results indicated that the catalyst contained a spinel crystal phase and an α-Fe$_2$O$_3$ crystal phase. The temperature programmed desorption test of ammonia showed that there were enhanced acid sites on the catalyst surface, and the specific surface area of the catalyst was 9 m$^2$/g.

Catalyst evaluation: The evaluation conditions of the catalyst were the same as those in Example 1. The yield per pass of butadiene was 79.4%, the conversion per pass of butene was 84.6%, and the selectivity of butadiene was 93.8%.

Example 4

Catalyst preparation; 5.13 g of Mg(NO$_3$)$_2$.6H$_2$O, 7.51 g of Al(NO$_3$)$_3$.9H$_2$O, 14.88 g of Zn(NO$_3$)$_2$.6H$_2$O and 112.48 g of Fe(NO$_3$)$_3$.9H$_2$O were dissolved in 250 ml of distilled water, and the preparation process of the catalyst was the same as that in Example 1. The resulting catalyst is denoted by D.

The composition and acid sites of the catalyst are shown in Table 1 and Table 2. XRD characterization results indicated that the catalyst contained a spinel crystal phase and an α-Fe$_2$O$_3$ crystal phase. The temperature programmed desorption test of ammonia showed that there were enhanced acid sites on the catalyst surface, and the specific surface area of the catalyst was 21 m$^2$/g.

Catalyst evaluation: The evaluation conditions of the catalyst were the same as those in Example 1. The yield per pass of butadiene was 78.8%, the conversion per pass of butene was 84.1%, and the selectivity of butadiene was 93.7%.

Example 5

Catalyst preparation: 2.57 g of Mg(NO$_3$)$_2$.6H$_2$O, 1.81 g of Cu(NO$_3$)$_2$.3H$_2$O, 18.77 g of Al(NO$_3$)$_3$.9H$_2$O, 4.46 g of Zn(NO$_3$)$_2$.6H$_2$O and 146.33 g of Fe(NO$_3$)$_3$.9H$_2$O were dissolved in 400 ml of distilled water. NaOH solution (1M) was added dropwise under quick stirring to obtain a pH value of 9.0 at the end of the precipitation. The remaining steps were the same as those in Example 1. The resulting catalyst is denoted by E.

The composition and acid sites of the catalyst are shown in Table 1 and Table 2. XRD characterization results indicated that the catalyst contained a spinel crystal phase and an α-Fe$_2$O$_3$ crystal phase. The temperature programmed desorption test of ammonia showed that there were enhanced acid sites on the catalyst surface, and the specific surface area of the catalyst was 30 m$^2$/g.

Catalyst evaluation: The evaluation conditions of the catalyst were the same as those in Example 1. The yield per pass of butadiene was 79.0%, the conversion per pass of butene was 82.9%, and the selectivity of butadiene was 95.3%.

Example 6

Catalyst preparation: 2.56 g of Mg(NO$_3$)$_2$.6H$_2$O, 1.74 g of Ni(NO$_3$)$_2$.6H$_2$O, 15.01 g of Al(NO$_3$)$_3$.9H$_2$O, 7.14 g of Zn(NO$_3$)$_2$.6H$_2$O and 153.42 g of Fe(NO$_3$)$_3$.9H$_2$O were dissolved in 400 ml of distilled water. NaOH solution (3M) was added dropwise to the metal ion solution to keep the pH at 9.2. The remaining steps were the same as those in Example 1. The resulting catalyst is denoted by F.

The composition and acid sites of the catalyst are shown in Table 1 and Table 2. XRD characterization results indicated that the catalyst contained a spinel crystal phase and an α-Fe$_2$O$_3$ crystal phase. The temperature programmed desorption test of ammonia showed that there were enhanced acid sites on the catalyst surface, and the specific surface area of the catalyst was 16 m$^2$/g.

Catalyst evaluation: The evaluation conditions of the catalyst were the same as those in Example 1. The yield per pass of butadiene was 83.8%, the conversion per pass of butene was 87.4%, and the selectivity of butadiene was 95.9%.

Example 7

Catalyst preparation: 2.54 g of Mg(NO$_3$)$_2$.6H$_2$O, 2.09 g of Ba(NO$_3$)$_2$, 14.25 g of Al(NO$_3$)$_3$.9H$_2$O, 7.44 g of Zn(NO$_3$)$_2$.6H$_2$O and 162.71 g of Fe(NO$_3$)$_3$.9H$_2$O were dissolved in 400 ml of distilled water to prepare a metal ion solution, and said metal ion solution was added dropwise into 400 ml of NaOH solution (3M) contained in a beaker under quick stirring so as to obtain a pH value of 9.5 at the end of the precipitation. The remaining steps were the same as those in Example 1, and the resulting catalyst is denoted by G.

The composition and acid sites of the catalyst are shown in Table 1 and Table 2. XRD characterization results indicated that the catalyst contained a spinel crystal phase and an α-Fe$_2$O$_3$ crystal phase. The temperature programmed desorption test of ammonia showed that there were enhanced acid sites on the catalyst surface, and the specific surface area of the catalyst was 17 m$^2$/g.

Catalyst evaluation: The evaluation conditions of the catalyst were the same as those in Example 1. The yield per pass of butadiene was 78.8%, the conversion per pass of butene was 82.2%, and the selectivity of butadiene was 95.9%.

Example 8

Catalyst preparation: 3.84 g of Mg(NO$_3$)$_2$.6H$_2$O, 2.54 g of Sr(NO$_3$)$_2$, 12.75 g of Al(NO$_3$)$_3$.9H$_2$O, 6.54 g of Zn(NO$_3$)$_2$.6H$_2$O and 158.63 g of Fe(NO$_3$)$_3$.9H$_2$O were dissolved in 400 ml of distilled water to prepare a metal ion solution. NaOH solution (3M) was added dropwise to the metal ion solution under quick stirring to obtain a pH value of 8.3 at the end of the precipitation. The remaining steps were the same as those in Example 1. The resulting catalyst is denoted by H.

The composition and acid sites of the catalyst are shown in Table 1 and Table 2. XRD characterization results indicated that the catalyst contained a spinel crystal phase and an α-Fe$_2$O$_3$ crystal phase. The temperature programmed desorption test of ammonia showed that there were enhanced acid sites on the catalyst surface, and the specific surface area of the catalyst was 34 m²/g.

Catalyst evaluation: The evaluation conditions of the catalyst were the same as those in Example 1. The yield per pass of butadiene was 82.6%, the conversion per pass of butene was 85.7%, and the selectivity of butadiene was 96.4%.

Example 9

Catalyst preparation: 2.55 g of Mg(NO$_3$)$_2$.6H$_2$O, 2.90 g of Co(NO$_3$)$_2$.6H$_2$O, 14.25 g of Al(NO$_3$)$_3$.9H$_2$O, 6.89 g of Zn(NO$_3$)$_2$.6H$_2$O and 161.78 g of Fe(NO$_3$)$_3$.9H$_2$O were dissolved in 400 ml of distilled water to prepare a metal ion solution. NaOH solution (3M) was added dropwise to the metal ion solution under quick stirring to obtain a pH value of 11.0 at the end of the precipitation. The remaining steps were the same as those in Example 1 and the resulting catalyst is denoted by I.

The composition and acid sites of the catalyst are shown in Table 1 and Table 2. XRD characterization results indicated that the catalyst contained a spinel crystal phase and an Fe$_2$O$_3$ crystal phase. The temperature programmed desorption test of ammonia showed that there were enhanced acid sites on the catalyst surface, and the specific surface area of the catalyst was 42 m²/g.

Catalyst evaluation: The evaluation conditions of the catalyst were the same as those in Example 1. The yield per pass of butadiene was 82.7%, the conversion per pass of butene was 86.1%, and the selectivity of butadiene was 96.0%.

Example 10

Catalyst preparation: 9.49 g of Mg(NO$_3$)$_2$.6H$_2$O, 3.75 g of Al(NO$_3$)$_3$.9H$_2$O, 7.44 g of Zn(NO$_3$)$_2$.6H$_2$O and 71.25 g of Fe(NO$_3$)$_3$.9H$_2$O were dissolved in 400 ml of distilled water to prepare a metal ion solution. NaOH solution (3M) was added dropwise to the metal ion solution under quick stirring. The pH value at the end of the precipitation was 9.3. The precipitate was heated for 60 minutes at 65° C. under stirring for it to be aged, and the remaining steps were the same as those Example 1. The resulting catalyst is denoted by J.

The composition and acid sites of the catalyst are shown in Table 1 and Table 2. XRD characterization results indicated that the catalyst contained a spinel crystal phase and an α-Fe$_2$O$_3$ crystal phase. The temperature programmed desorption test of ammonia showed that there were enhanced acid sites on the catalyst surface, and the specific surface area of the catalyst was 22 m²/g.

Catalyst evaluation: The evaluation conditions of the catalyst were the same as those in Example 1. The yield per pass of butadiene was 79.0%, the conversion per pass of butene was 85.3%, and the selectivity of butadiene was 92.6%.

Catalyst preparation: 2.42 g of Cu(NO$_3$)$_2$.3H$_2$O, 2.33 g of Ni(NO$_3$)$_2$.6H$_2$O, 14.25 g of Al(NO$_2$)$_3$.9H$_2$O, 7.44 g of Zn(NO$_3$)$_2$.6H$_2$O and 12.5.62 g of Fe(NO$_3$)$_3$.9H$_2$O were dissolved in 400 ml of distilled water to prepare a metal ion solution. NaOH solution (3M) was added dropwise to the metal ion solution under quick stirring to obtain a pH value of 8.6 at the end of the precipitation. The resulting precipitate was heated for 30 minutes at 65° C. under stirring for it to be aged, and the remaining steps were the same as those in Example 1. The resulting catalyst is denoted by K.

The composition and acid sites of the catalyst are shown in Table 1 and Table 2. XRD characterization results indicated that the catalyst contained a spinel crystal phase and an α-Fe$_2$O$_3$ crystal phase. The temperature programmed desorption test of ammonia showed that there were enhanced acid sites on the catalyst surface, and the specific surface area of the catalyst was 29 m²/g.

The resulting catalyst was analyzed by an ICP-AES inductively coupled plasma emission spectrometer, and the results are as follows: Cu: 2.06 wt %, Ni: 1.95 wt %, Al: 3.41 wt %, Zn: 5.27 wt %, Fe: 57.8 wt %.

Catalyst evaluation: The evaluation conditions of the catalyst were the same as those in Example 1. The yield per pass of butadiene was 81.7%, the conversion per pass of butene was 85.7%, and the selectivity of butadiene was 95.3%.

Example 12

Catalyst preparation: 2.42 g of Cu(NO$_3$)$_2$.3H$_2$O, 2.74 g of Ba(NO$_3$)$_2$, 9.38 g of Al(NO$_3$)$_3$.9H$_2$O, 7.14 g of Zn(NO$_3$)$_2$.6H$_2$O and 167.53 g of Fe(NO$_3$)$_3$.9H$_2$O were dissolved in 400 ml of distilled water to prepare a metal ion solution. NaOH solution (3M) was added dropwise to the metal ion solution under quick stirring to obtain a pH value of 9.8 at the end of precipitation. The resulting precipitate was heated for 90 minutes at 65° C. under stirring for it to be aged, stood at room temperature for 24 hours, and then filtered. The resulting filter cake was washed with distilled water, and the remaining steps were the same as those in Example 1. The resulting catalyst is denoted by L.

The composition and acid sites of the catalyst are shown in Table 1 and Table 2. XRD characterization results indicated that the catalyst contained a spinel crystal phase and an α-Fe$_2$O$_3$ crystal phase. The temperature programmed desorption test of ammonia showed that there were enhanced acid sites on the catalyst surface, and the specific surface area of the catalyst was 36 m²/g.

Catalyst evaluation: The evaluation conditions of the catalyst were the same as those in Example 1. The yield per pass of butadiene was 83.0%, the conversion per pass of butene was 85.8%, and the selectivity of butadiene was 96.7%.

Example 13

Catalyst preparation: 3.49 g of Co(NO$_3$)$_2$.6H$_2$O, 3.34 g of Ni(NO$_3$)$_2$.6H$_2$O, 11.63 g of Al(NO$_3$)$_3$.9H$_2$O, 8.92 g of Zn(NO$_3$)$_2$.6H$_2$O and 167.22 g of Fe(NO$_3$)$_3$.9H$_2$O were dissolved in 400 ml of distilled water to prepare a metal ion solution. NaOH solution (3M) was added dropwise to the metal ion solution under quick stirring to obtain a pH value of 9.5 at the end of the precipitation. The resulting precipitate was heated for 90 minutes at 65° C. under stirring for it to be aged, stood at room temperature for 12 hours, and then filtered. The resulting filter cake was washed with distilled water. After being dried at 120° C. for 24 hours, the filter cake was placed into a muffle furnace with a furnace temperature of 650° C. and calcined for 6 hours. The remaining steps are the same as those in Example 1. The resulting catalyst is denoted by M.

The composition and acid sites of the catalyst are shown in Table 1 and Table 2. XRD characterization results indicated that the catalyst contained spinel crystal a phase and an α-Fe$_2$O$_3$ crystal phase. The temperature programmed desorption test of ammonia showed that there were enhanced acid sites on the catalyst surface, and the specific surface area of the catalyst was 27 m²/g.

Catalyst evaluation: The evaluation conditions of the catalyst were the same as those in Example 1. The yield per pass of butadiene was 83.2%, the conversion per pass of butene was 85.3%, and the selectivity of butadiene was 97.5%.

Example 14

Catalyst preparation: 4.72 g of Ca(NO$_3$)$_2$.4H$_2$O, 10.87 g of Cu(NO$_3$)$_2$.3H$_2$O, 7.50 g of Al(NO$_3$)$_3$.9H$_2$O, 7.73 g of Zn(NO$_3$)$_2$.6H$_2$O and 188.21 g of Fe(NO$_3$)$_3$.9H$_2$O were dissolved in 400 ml of distilled water to prepare a metal ion solution. NaOH solution (3M) was added dropwise to the metal ion solution under quick stirring to obtain a pH value of 9.3 at the end of the precipitation. The precipitate was heated for 90 minutes at 65° C. under stirring for it to be aged, stood at room temperature for 12 hours, and then filtered. The resulting filter cake was washed with distilled water. After being dried at 120° C. for 24 hours, the filter cake was placed into a muffle furnace with a furnace temperature of 650° C. and calcined for 10 hours. The remaining steps are the same as those in Example 1. The resulting catalyst is denoted by N.

The composition and acid sites of the catalyst are shown in Table 1 and Table 2. XRD characterization results indicated that the catalyst contained a spinel crystal phase and an α-Fe$_2$O$_3$ crystal phase. The temperature programmed desorption test of ammonia showed that there were enhanced acid sites on the catalyst surface, and the specific surface area of the catalyst was 26 m²/g.

Catalyst evaluation: The evaluation conditions of the catalyst were the same as those in Example 1. The yield per pass of butadiene was 82.6%, the conversion per pass of butene was 86.9%, and the selectivity of butadiene was 95.1%.

Example 15

Catalyst preparation: 5.13 g of Mg(NO$_3$)$_2$.6H$_2$O, 2.81 g of Be(NO$_3$)$_2$.3H$_2$O, 9.38 g of Al(NO$_3$)$_3$.9H$_2$O, 7.14 g of Zn(NO$_3$)$_2$.6H$_2$O and 158.60 g of Fe(NO$_3$)$_3$.9H$_2$O were dissolved in 400 ml of distilled water to prepare a metal ion solution. Ammonia solution (15 wt %) was added dropwise to the metal ion solution under quick stirring to obtain a pH value of 10.5 at the end of the precipitation. The remaining steps were the same as those in Example 1, and the resulting catalyst is denoted by O.

The composition and acid sites of the catalyst are shown in Table 1 and Table 2. XRD characterization results indicated that the catalyst contained a spinel crystal phase and an αFe$_2$O$_3$ crystal phase. The temperature programmed desorption test of ammonia showed that there were enhanced acid sites on the catalyst surface, and the specific surface area of the catalyst was 16 m²/g.

Catalyst evaluation: The evaluation conditions of the catalyst were the same as those in Example 1. The yield per pass of butadiene was 79.2%, the conversion per pass of butene was 84.1%, and the selectivity of butadiene was 94.2%.

Example 16

Catalyst preparation: 6.41 g of Mg(NO$_3$)$_2$.6H$_2$), 18.76 g of Al(NO$_3$)$_3$.9H$_2$O and 163.67 g of Fe(NO$_3$)$_3$.9H$_2$O were dissolved in 400 ml of distilled water to prepare a metal ion solution, and the remaining steps were the same as those in Example 1. The resulting catalyst is denoted by P.

The composition and acid sites of the catalyst are shown in Table 1 and Table 2. XRD characterization results indicated that the catalyst contained a spinel crystal phase and an α-Fe$_2$O$_3$ crystal phase. The temperature programmed desorption test of ammonia showed that there were enhanced acid sites on the catalyst surface, and the specific surface area of the catalyst was 28 m²/g.

Catalyst evaluation: The evaluation conditions of the catalyst were the same as those in Example 1. The yield per pass of butadiene was 76.9%, the conversion per pass of butene was 82.2%, and the selectivity of butadiene was 93.5%.

Example 17

Catalyst preparation: 4.73 g of Ca(NO$_3$)$_2$.4H$_2$O, 2.56 g of Mg(NO$_3$)$_2$.6H$_2$O, 7.50 g of Al(NO$_3$)$_3$.9H$_2$O, 11.90 g of Zn(NO$_3$)$_2$.6H$_2$O and 231.45 g of Fe(NO$_3$)$_3$.9H$_2$O were weighed, and the remaining steps were the same as those in Example 1. The resulting catalyst is denoted by Q.

The composition and acid sites of the catalyst are show en in Table 1 and Table 2. XRD characterization results indicated that the catalyst contained a spinel crystal phase and an α-Fe$_2$O$_3$ crystal phase. The temperature programmed desorption test of ammonia showed that there were enhanced acid sites on the catalyst surface, and the specific surface area of the catalyst was 32 m²/g.

Catalyst evaluation: The evaluation conditions of the catalyst were the same as those in Example 1. The yield per pass of butadiene was 81.9%, the conversion per pass of butene was 85.1%, and the selectivity of butadiene was 96.2%.

Example 18

Catalyst preparation: 2.50 g of Mn(NO$_3$)$_2$.4H$_2$O, 7.69 g of Mg(NO$_3$)$_2$.6H$_2$O, 15.00 g of Al(NO$_3$)$_3$.9H$_2$O and 237.78 g of Fe(NO$_3$)$_3$.9H$_2$O were weighed, and the remaining steps were the same as those in Example 1. The resulting catalyst is denoted by R.

The composition and acid sites of the catalyst are shown in Table 1 and Table 2. XRD characterization results indicated that the catalyst contained a spinel crystal phase and an α-Fe$_2$O$_3$ crystal phase. The temperature programmed desorption test of ammonia showed that there were enhanced acid sites on the catalyst surface, and the specific surface area of the catalyst was 41 m²/g.

Catalyst evaluation: The evaluation conditions of the catalyst were the same as those in Example 1. The yield per pass of butadiene was 77.6%, the conversion per pass of butene was 81.9%, and the selectivity of butadiene was 94.7%.

Example 19

Catalyst preparation: 1.45 g of Ni(NO$_3$)$_2$.6H$_2$O, 1.46 g of Co(NO$_3$)$_2$.6H$_2$O, 3.85 g of Mg(NO$_3$)$_2$.6H$_2$O, 11.25 g of Al(NO$_3$)$_3$.9H$_2$O, 8.92 g of Zn(NO$_3$)$_2$.6H$_2$O and 175.11 g of Fe(NO$_3$)$_3$.9H$_2$O were weighed, and the remaining steps were the same as those in Example 1. The resulting catalyst is denoted by S.

The composition and acid sites of the catalyst are shown in Table 1 and Table 2. XRD characterization results indicated that the catalyst contained a spinel crystal phase and an α-Fe$_2$O$_3$ crystal phase. The temperature programmed desorption test of ammonia showed that there were enhanced acid sites on the catalyst surface, and the specific surface area of the catalyst was 20 m²/g.

Catalyst evaluation: The evaluation conditions of the catalyst were the same as those in Example 1. The yield per pass of butadiene was 80.4%, the conversion per pass of butene was 84.7%, and the selectivity of butadiene was 94.9%.

TABLE 1

| Catalyst | Element M | a (or a') | b (or b') | c (or c') | e (or 2) | f (or 4) | Z |
|---|---|---|---|---|---|---|---|
| Example 1: A | Mg | 2.50 | 1.00 | 1.00 | 10.00 | 20.00 | 54.3% |
| Example 2: B | Mg | 0.50 | 1.00 | 0.50 | 5.00 | 10.00 | 64.0% |
| Example 3: C | Mg | 7.00 | 1.00 | 1.50 | 20.00 | 40.00 | 46.4% |
| Example 4: D | Mg | 2.50 | 1.00 | 1.00 | 10.00 | 20.00 | 22.3% |
| Example5: E | Mg, Cu | 0.30 | 1.00 | 0.35 | 4.00 | 8.15 | 38.4% |
| Example 6: F | Mg, Ni | 0.60 | 1.00 | 0.40 | 5.00 | 10.00 | 40.8% |
| Example 7: G | Mg, Ba | 0.66 | 1.00 | 0.47 | 5.26 | 10.53 | 42.9% |
| Example 8: H | Mg, Sr | 0.65 | 1.00 | 0.79 | 5.88 | 11.76 | 41.9% |
| Example 9: I | Mg, Co | 0.61 | 1.00 | 0.53 | 5.26 | 10.53 | 43.3% |
| Example 10: J | Mg | 2.50 | 1.00 | 3.70 | 3.00 | 12.20 | 64.5% |
| Example 11: K | Cu, Ni | 0.66 | 1.00 | 0.47 | 5.26 | 10.52 | 29.4% |
| Example 12: L | Cu, Ba | 0.96 | 1.00 | 0.82 | 8.00 | 15.28 | 44.2% |
| Example 13: M | Co, Ni | 0.97 | 1.00 | 0.76 | 6.45 | 12.90 | 44.0% |
| Example 14: N | Ca, Cu | 1.30 | 1.00 | 3.25 | 10.00 | 21.05 | 47.1% |
| Example 15: O | Mg, Be | 0.96 | 1.00 | 1.40 | 8.00 | 15.86 | 43.0% |
| Example 16: P | Mg | 0 | 1.00 | 0.50 | 4.00 | 8.00 | 45.6% |
| Example 17: Q | Mg, Ca | 2.00 | 1.00 | 1.50 | 10.00 | 20.00 | 57.8% |
| Example 18: R | Mg, Mn | 0 | 1.00 | 1.00 | 5.00 | 10.00 | 61.6% |
| Example 19: S | Mg, Ni, Co | 1.00 | 1.00 | 0.83 | 6.67 | 13.33 | 46.7% |
| Comparative Example 1 | Mg | 0.60 | 0 | 0.40 | 2.00 | 4.00 | 55.5% |
| Comparative Example 2 | Cu, Ba | 0.60 | 0 | 0.40 | 2.00 | 4.00 | 42.8% | drogenation reaction of butene to butadiene at a temperature of 340° C., a space velocity of butene of 350 h⁻¹, a molar ratio of oxygen-butene of 0.70:1 and a molar ratio of water-butene of 10:1; the yield per pass of butadiene was 79.2%, the conversion per pass of butene was 82.6%, and the selectivity of butadiene was 95.9%.

Example 21

The catalyst of Example 1 was activated for 1 hour with air in a fixed bed reactor at 470° C. After cooling, the resulting catalyst was used to catalyze the oxidative dehydrogenation reaction of butene to butadiene at a temperature of 380° C., a space velocity of butene of 350 h⁻¹, a molar ratio of oxygen-butene of 0.70:1, and a molar ratio of water-butene of 10:1; the yield per pass of butadiene was 81.8%, the conversion per pass of butene was 87.1%, and the selectivity of butadiene was 93.9%.

Example 22

The catalyst of Example 1 was activated for 1 h with air in a fixed bed reactor at 470° C. After cooling, the resulting catalyst was used to catalyze the oxidative dehydrogenation reaction of butene to butadiene at a temperature of 360° C., a space velocity of butene of 300 h⁻¹, a molar ratio of oxygen-butene of 0.70:1 and a molar ratio of water-butene of 10:1; the yield per pass of butadiene was 79.3%, the conversion per pass of butene was 86.9%, and the selectivity of butadiene was 91.1%.

Example 23

The catalyst of Example 1 was activated for 1 hour with air in a fixed bed reactor at 470° C. After cooling, the

TABLE 2

| | | Position of NH₃ Desorption peaks (Acid sites) (° C.) | | |
|---|---|---|---|---|
| Catalyst | | Desorption peak 1 (full width at half maximum) | Desorption peak 2 (full width at half maximum) | Desorption peak 3 (full width at half maximum) |
| Example 1 | A | 188.5 (87.9) | 278.8 (56.4) | 361.4 (81.6) |
| Example 2 | B | 186.2 (85.2) | 275.2 (61.5) | 366.6 (87.3) |
| Example 3 | C | 176.5 (90.4) | 270.4 (54.2) | 359.2 (84.5) |
| Example 4 | D | 195.3 (94.5) | 288.8 (58.9) | 355.9 (75.8) |
| Example 5 | E | 190.2 (86.9) | 278.0 (50.4) | 367.8 (74.4) |
| Example 6 | F | 202.3 (80.8) | 289.4 (57.2) | 365.2 (86.5) |
| Example 7 | G | 184.9 (77.9) | 294.3 (63.5) | 374.5 (94.6) |
| Example 8 | H | 178.6 (83.5) | 296.1 (55.1) | 366.3 (95.2) |
| Example 9 | I | 186.6 (84.0) | 285.9 (57.2) | 384.2 (86.7) |
| Example 10 | J | 192.0 (79.4) | 278.2 (50.6) | 381.4 (77.4) |
| Example 11 | K | 175.9 (92.6) | 270.5 (48.6) | 395.0 (72.0) |
| Example 12 | L | 188.0 (76.2) | 266.1 (59.2) | 364.2 (69.4) |
| Example 13 | M | 194.4 (83.6) | 273.5 (66.0) | 370.5 (80.5) |
| Example 14 | N | 186.5 (88.4) | 284.6 (57.8) | 348.2 (64.2) |
| Example 15 | O | 181.2 (86.9) | 278.6 (48.9) | 365.5 (88.0) |
| Example 16 | P | 195.8 (92.5) | 274.5 (56.6) | 374.2 (80.3) |
| Example 17 | Q | 196.4 (84.4) | 280.9 (47.8) | 369.1 (79.2) |
| Example 18 | R | 193.4 (76.8) | 271.1 (51.6) | 365.2 (90.4) |
| Example 19 | S | 187.9 (85.6) | 265.0 (57.0) | 366.4 (86.4) |
| Comparative Example 1 | / | 189.5 (85.1) | 275.8 (58.6) | — |
| Comparative Example 2 | / | 187.8 (86.7) | 277.3 (59.2) | — |

Example 20

The catalyst of Example 1 was activated for 1 hour with air in a fixed bed reactor at 470° C. After cooling, the resulting catalyst was used to catalyze the oxidative dehydrogenation reaction of butene to butadiene at a temperature of 360° C., a space velocity of butene of 350 h⁻¹, a molar ratio of oxygen-butene of 0.80:1 and a molar ratio of water-butene of 10:1; the yield per pass of butadiene was 82.1%, the conversion per pass of butene was 87.7%, and the selectivity of butadiene was 93.6%.

Example 24

The catalyst of Example 1 was activated for 1 hour with air in a fixed bed reactor at 470° C. After cooling, the resulting catalyst was used to catalyze the oxidative dehydrogenation reaction of butene to butadiene at a temperature of 360° C., a space velocity of butene of 350 h$^{-1}$, a molar ratio of oxygen-butene of 0.70:1 and a molar ratio of water-butene of 12:1; the yield per pass of butadiene was 80.0%, the conversion per pass of butene was 85.3%, and the selectivity of butadiene was 92.6%.

Example 25

The stability of the catalyst of Example 1 was studied; the evaluation conditions of the catalyst were the same as those in Example 1; and the results are shown in Table 3.

TABLE 3

| Reaction time (h) | Conversion of butene (%) | Selectivity to butadiene (wt. %) |
| --- | --- | --- |
| 100 | 85.9 | 93.3 |
| 3,000 | 85.8 | 93.4 |
| 6,000 | 85.6 | 93.1 |

As the data in Table 3 shows, when the catalyst of the present disclosure was used to catalyze the oxidative dehydrogenation reaction of butene to butadiene, the catalyst not only provided high catalytic activity and selectivity but also retained high stability, wherein the catalyst life was at least more than 6,000 hours.

Comparative Example 1

Catalyst preparation: 10.26 g of Mg(NO$_3$)$_2$.6H$_2$O, 17.85 g of Zn(NO$_3$)$_2$.6H$_2$O and 216.45 g of Fe(NO$_3$)$_3$.9H$_2$O were dissolved in 500 ml of distilled water, and NaOH solution (3M) was added dropwise under quick stirring to obtain a pH value of 9.3 at the end of the precipitation. The resulting precipitate was heated at 65° C. for 90 minutes under stirring for it to be aged, stood at room temperature for 12 hours, and then filtered. The resulting filter cake was washed with distilled water. After being dried at 120° C. for 24 hours, the filter cake was placed into a muffle furnace with a furnace temperature of 650° C. and calcined for 6 hours.

The composition and acid sites of the catalyst are shown in Table 1 and Table 2. XRD characterization results indicated that the catalyst contained a spinel crystal phase and an α-Fe$_2$O$_3$ crystal phase; temperature programmed desorption test of ammonia showed that there were not enhanced acid sites on the catalyst surface, and the specific surface area of the catalyst was 26 m$^2$/g. In Table 1, Comparative Example 1 or Comparative Example 2 does not have the values of a, b, c, e and f. Rather, the values in the Comparative Example 1 or Comparative Example 2 correspond to a', b', c', 2 and 4.

Catalyst evaluation: The evaluation conditions of the catalyst were the same as those in Example 1. The yield per pass of butadiene was 74.9%, the conversion per pass of butene was 79.9%, and the selectivity of butadiene was 93.7%.

Stability of the catalyst: The stability of the catalyst was studied under the same evaluation conditions as in Example 1. The results are shown in Table 4.

TABLE 4

| Reaction time (h) | Conversion of butene (%) | Selectivity to butadiene (wt. %) |
| --- | --- | --- |
| 100 | 79.7 | 92.2 |
| 1,000 | 76.6 | 91.4 |
| 1,800 | 70.3 | 90.9 |

Comparative Example 2

Catalyst preparation: 4.83 g of Cu(NO$_3$)$_2$.3H$_2$O, 5.23 g of Ba(NO$_3$)$_2$, 17.85 g of Zn(NO$_3$)$_2$.6H$_2$O and 177.53 g of Fe(NO$_3$)$_3$.9H$_2$O were dissolved in 400 ml of distilled water, and NaOH solution (3M) was added dropwise under quick stirring to obtain a pH value of 9.3 at the end of the precipitation. The resulting precipitate was heated for 90 minutes at 65° C. under stirring for it to be aged, stood at room temperature for 12 hours, and then filtered. The resulting filter cake was washed with distilled water, and the remaining steps were the same as those in Example 1.

The composition and acid sites of the catalyst are shown in Table 1 and Table 2. XRD characterization results indicated that the catalyst contained a spinel crystal phase and an α-Fe$_2$O$_3$ crystal phase. The temperature programmed desorption test of ammonia showed that there were no enhanced acid sites on the catalyst surface, and the specific surface area of the catalyst was 20 m$^2$/g.

Catalyst evaluation: The evaluation conditions of the catalyst are the same as those in Example 1. The yield per pass of butadiene was 72.5%, the conversion per pass of butene was 78.4%, and the selectivity of butadiene was 92.5%.

Stability of the catalyst: The stability of the catalyst was studied under the same evaluation conditions as in Example 1, and the results are shown in Table 5.

TABLE 5

| Reaction time (h) | Conversion of butene (%) | Selectivity to butadiene (wt. %) |
| --- | --- | --- |
| 100 | 78.4 | 92.5 |
| 1,000 | 76.7 | 91.3 |
| 1,800 | 71.2 | 90.4 | it can be seen from the evaluation results of the catalyst in Comparative Examples 1 and 2 and data in Table 4 and Table 5, when the catalysts of the Comparative Examples were used to catalyze the oxidative dehydrogenation reaction of butene to butadiene, the comparative catalysts presented lower catalytic activity and lower selectivity to the desired product than the catalysts provided in the present disclosure. Most importantly, the catalytic activity and selectivity of the catalysts in Comparative Examples 1 and 2 dropped sharply after 1,800 hours of reaction, but the catalytic activity and selectivity of the catalyst of the present disclosure remained at a high level after 6,000 hours of reaction time, which shows that the catalysts of the present disclosure possess high stability.

What is claimed is:
1. A catalyst for the oxidative dehydrogenation of butene to butadiene comprising at least one compound of formula Zn$_a$Al$_b$M$_c$Fe$_e$O$_f$Z(α-Fe$_2$O$_3$), wherein M is at least one element chosen from Be, Mg, Ca, Sr, Mn, Ba, Cu, Co, and Ni; Z is the percentage by weight of α-$Fe_2O_3$ in the catalyst, ranging from 10% to 70%; wherein b is 1, a ranges from 0 to 10, c is larger than zero and less than or equal to 4, e ranges from 3 to 25, f is greater than 4.5 and equal to or less than 48; and further wherein 2a+3b+2c+3e=2f.

2. The catalyst according to claim 1, wherein the catalyst comprises a spinel crystal phase and an α-$Fe_2O_3$ crystal phase, and the specific surface area of the catalyst ranges from 1 $m^2/g$ to 80 $m^2/g$.

3. The catalyst according to claim 1, wherein M is at least two elements chosen from Be, Mg, Ca, Sr, Mn, Ba, Cu, Co, and Ni.

4. The catalyst according to claim 1, wherein a is not zero.

5. The catalyst according to claim 1, wherein e ranges from 3 to 20.

6. The catalyst according to claim 1, wherein temperature programmed desorption spectrum of ammonia probe molecules from said catalyst comprises a characteristic peak at desorption temperatures of 340° C. to 400° C. and full width at half maximum of 60° C. to 100° C.

7. The catalyst according to the claim 6, wherein the temperature programmed desorption spectrum of ammonia probe molecules from said catalyst further comprises (i) a characteristic peak at desorption temperatures of 170° C. to 210° C. and full width at half maximum of 70° C. to 100° C., and (ii) a characteristic peak at desorption temperatures of 260° C. to 300° C. and full width at half maximum of 40° C. to 70° C.

8. A process for preparing the catalyst according to claim 1, comprising:
   (1) preparing a salt solution comprising Al, M, and Fe, and optionally the element of Zn,
   (2) adding a base solution to the salt solution to obtain a pH value ranging from 8 to 12, and
   (3) aging, drying and calcining the precipitate obtained from (2).

9. The process according to claim 8, comprising:
   an aging temperature ranging from 5° C. to 80° C.,
   an aging time ranging from 0.5 hour to 48 hours,
   a calcination temperature ranging from 500° C. to 900° C., and
   a calcination time ranging from 3 hours to 72 hours.

10. A process for the oxidative dehydrogenation of butene to butadiene comprising: adding the catalyst prepared by the process according to claim 8 into oxidative dehydrogenation reaction of butene to butadiene, with butene, oxygen-containing gas, and water vapor.

11. The process according to claim 10, wherein the reaction is carried out at a temperature ranging from 300° C. to 500° C., a space velocity ranging from 200 $h^{-1}$ to 500 $h^{-1}$, a molar ratio of oxygen-butene ranging from 0.6:1 to 0.9:1, and a molar ratio of water-butene ranging from 6:1 to 20:1.

12. A process for the oxidative dehydrogenation of butene to butadiene comprising: adding the catalyst according to claim 1 into oxidative dehydrogenation reaction of butene to butadiene, with butene, oxygen-containing gas, and water vapor.

13. The process according to claim 12, wherein the reaction is carried out at a temperature ranging from 300° C. to 500° C., a space velocity ranging from 200 $h^{-1}$ to 500 $h^{-1}$, a molar ratio of oxygen-butene ranging from 0.6:1 to 0.9:1, and a molar ratio of water-butene ranging from 6:1 to 20:1.

* * * * *